(12) United States Patent
Conti et al.

(10) Patent No.: US 11,560,726 B2
(45) Date of Patent: Jan. 24, 2023

(54) METHOD AND DEVICE FOR PRE-CASTING CONDUIT HOLES IN BUILDING FOUNDATIONS

(71) Applicants: Tommaso Conti, Nantucket, MA (US); Robert Aschwanden, Siasconset, MA (US); Morgan Forger, Nantucket, MA (US)

(72) Inventors: Tommaso Conti, Nantucket, MA (US); Robert Aschwanden, Siasconset, MA (US); Morgan Forger, Nantucket, MA (US)

( * ) Notice: Subject to any disclaimer, the term of this patent is extended or adjusted under 35 U.S.C. 154(b) by 0 days.

(21) Appl. No.: 17/027,678

(22) Filed: Sep. 21, 2020

(65) Prior Publication Data

US 2021/0087770 A1    Mar. 25, 2021
US 2022/0349142 A9    Nov. 3, 2022

Related U.S. Application Data

(60) Provisional application No. 62/902,985, filed on Sep. 20, 2019.

(51) Int. Cl.
| | |
|---|---|
| *E04G 15/06* | (2006.01) |
| *E02D 5/68* | (2006.01) |
| *E02D 5/18* | (2006.01) |
| *A61M 60/531* | (2021.01) |
| *A61M 60/414* | (2021.01) |
| *A61M 60/808* | (2021.01) |

(52) U.S. Cl.
CPC ........... *E04G 15/06* (2013.01); *A61M 60/414* (2021.01); *A61M 60/531* (2021.01); *A61M 60/808* (2021.01); *E02D 5/182* (2013.01); *E02D 5/68* (2013.01); *E02D 2250/0007* (2013.01); *E02D 2250/0023* (2013.01); *E02D 2300/0001* (2013.01); *E02D 2300/002* (2013.01); *E02D 2300/0007* (2013.01); *E02D 2300/0009* (2013.01); *E02D 2300/0014* (2013.01); *E02D 2300/0046* (2013.01); *E02D 2300/0071* (2013.01)

(58) Field of Classification Search
CPC ....... E04G 15/00; E04G 15/06; E04G 15/063; E04G 15/068
USPC .................. 52/220.8, 741.13; 249/34, 39–46
See application file for complete search history.

(56) References Cited

U.S. PATENT DOCUMENTS

| | | | | |
|---|---|---|---|---|
| 3,523,552 A | * | 8/1970 | Ogden | E04G 15/061 137/592 |
| 4,159,099 A | * | 6/1979 | Maguire | E04G 15/061 249/177 |
| 4,619,087 A | * | 10/1986 | Harbeke | E04G 15/061 285/64 |

(Continued)

FOREIGN PATENT DOCUMENTS

| | | | |
|---|---|---|---|
| KR | 101317440 B1 | * | 10/2013 |
| KR | 200469370 Y1 | * | 10/2013 |
| KR | 2015140124 A | * | 12/2015 |

*Primary Examiner* — Frederick L Lagman
(74) *Attorney, Agent, or Firm* — Daniel N. Smith

(57) ABSTRACT

A method of constructing multiple conduits in building foundations that eliminates the process of core drilling after the foundation has been poured and set. This method creates optional openings for possible future connections. The process uses removable conduit molds installed before the foundation is poured. Once the foundation has set, conduit molds are removed to explose conduits in the foundation as needed.

14 Claims, 17 Drawing Sheets

(56) References Cited

U.S. PATENT DOCUMENTS

| | | | | |
|---|---|---|---|---|
| 4,623,170 A | * | 11/1986 | Cornwall | E04G 15/061 |
| | | | | 249/177 |
| 5,405,119 A | * | 4/1995 | Maguire | B28B 7/18 |
| | | | | 249/183 |
| 6,530,187 B2 | * | 3/2003 | Shimizu | F16L 5/02 |
| | | | | 52/220.1 |
| 2004/0016190 A1 | * | 1/2004 | Radke | E04G 15/061 |
| | | | | 52/232 |
| 2008/0073480 A1 | * | 3/2008 | Lesmeister | E04G 13/00 |
| | | | | 249/34 |

* cited by examiner

4

METHOD AND DEVICE FOR PRE-CASTING CONDUIT HOLES IN BUILDING FOUNDATIONS

CROSS REFERENCE TO RELATED APPLICATION

This application claims priority to and the benefit of U.S. Provisional Patent Application No. 62/902,985 filed on Sep. 20, 2019, the contents of which are incorporated herein by reference.

FIELD OF THE INVENTION

The invention relates to a device and method that pre-casts conduit holes in residential and commercial building foundations for immediate, or future use.

BACKGROUND OF INVENTION

Residential and commercial building foundations require multiple watertight openings from the interior of the foundation to the exterior of the foundation, below grade, to permit the uninterrupted passage of various power and fluid conduits. These conduits may include, but are not limited to: conduits for power lines to main panel and subpanels, low voltage lines, cable lines, telephone lines, water supply lines, sewage lines, line sets condensers, heat pumps, power lines to condensers, generator lines, and pool equipment. These conduits typical range in diameter from 1.25" for water lines to 8" for sewage or septic lines. These conduits may range from 18" below grade, for power conduits, to 48" below grade for water conduits, to even further below grade for sewer or septic conduits. Building constructions may have multiple conduits on multiple different locations of the foundation.

In typical building construction, these openings for conduits are created after the rebar-enforced concrete foundation has set. The locations of the conduits are determined in the foundation, and a core drill, drills the appropriate size conduit holes into the foundation from the interior side to the exterior side. Costs for each conduit hole to be drilled can run high, adding significantly to building costs.

Furthermore, use of the core drill to drill foundation conduit holes is cumbersome. The core drill is a heavy duty machine which must be bolted to the foundation wall, and supplied power and water for operation. The core drill utilizes diamond bits which are costly to replace. If the core drill encounters rebar within the foundation wall, it will significant shorten the life of the core drill bits.

Once the conduit holes are drilled, a cylindrical conduit is placed within the hole. A watertight seal is created around the conduit using a link seal which contains a plurality of links and a gasket. As you tighten the link seal, the links compress the gasket to create a tight fitting between the concrete foundation and the conduit. To save on costs, some construction completes the conduit seal with sprayed foam or cement. Both of these methods will deteriorate or crack over time, resulting in a loose conduit connection.

It is an object of the present invention to overcome or substantially ameliorate at least some of the disadvantages of conventional construction techniques through the development of a pre-cast mold for creating conduit holes in building foundations.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses a construction system for pre-casting conduit holes in a building foundation, the system comprising: a plurality of concrete molds installed around the building foundation, wherein the plurality of concrete molds are configured to support a poured foundation concrete mix; a plurality of lightweight conduit molds installed within the plurality of concrete molds at locations designated for conduits within the building foundation; wherein each conduit mold comprises a unitary cylindrical bar, a cylindrical central ring surrounding the cylindrical bar, and a rubber surface on each end of the cylindrical bar; wherein the foundation concrete mix is poured in the plurality of concrete forms around the plurality of conduit molds and sets; wherein the plurality of concrete forms are removed, and the rubber surfaces on each end of each cylindrical bar are substantially flush with an interior and exterior wall of the building foundation; and removing the conduit mold from the building foundation to open a conduit hole, and installing a conduit within the conduit hole in the foundation wall.

The subject invention discloses a construction system for pre-casting conduit holes in a building foundation, the system comprising: a plurality of foundation concrete molds installed around a designated location of the building foundation, wherein the plurality of foundation concrete molds are configured to support a poured foundation concrete mix that will form the building foundation walls; a plurality of lightweight conduit molds installed within the plurality of foundation concrete molds in a unique order of locations designated for conduits within the building foundation; wherein each conduit mold comprises a unitary cylindrical shape, a cylindrical central ring surrounding the cylindrical shape, and a rubber surface on each end of the cylindrical shape; wherein the foundation concrete mix is poured in the plurality of foundation concrete forms around the plurality of conduit molds and sets; wherein the foundation concrete mix sets to form the building foundation walls and simultaneously form the conduit holes at each of the plurality of concrete molds, wherein the plurality of foundation concrete forms are removed, and the rubber surfaces on each end of each cylindrical shape are substantially flush with interior and exterior surfaces of the building foundation walls; and removing the conduit mold from the building foundation to open a conduit hole without either vibrating, drilling, hammering, or chiseling the building foundation or the foundation walls, and installing a conduit within the conduit hole in the foundation wall.

The subject invention discloses a construction system for pre-casting conduit holes in a building foundation, the system comprising: a plurality of foundation concrete molds installed around a designated location of the building foundation, wherein the plurality of foundation concrete molds are configured to support a poured foundation concrete mix that will form the building foundation walls; a plurality of lightweight conduit molds installed within the plurality of foundation concrete molds in a unique order of locations designated for conduits within the building foundation; wherein each conduit mold comprises a unitary cylindrical shape, a cylindrical central ring surrounding the cylindrical shape, and a rubber surface on each end of the cylindrical shape; wherein the foundation concrete mix is poured in the plurality of foundation concrete forms around the plurality of conduit molds and sets; wherein the foundation concrete mix sets to form the building foundation walls and simultaneously form the conduit holes at each of the plurality of concrete molds, wherein the plurality of foundation concrete forms are removed, and the rubber surfaces on each end of each cylindrical shape are substantially flush with interior and exterior surfaces of the building foundation walls; and removing the conduit mold from the building foundation to open a conduit hole without drilling the building foundation or the foundation walls, and installing a conduit within the conduit hole in the foundation wall.

The subject invention discloses a construction system for pre-casting conduit holes in a building foundation, the system comprising: a plurality of foundation concrete molds installed around a designated location of the building foundation, wherein the plurality of foundation concrete molds are configured to support a poured foundation concrete mix that will form the building foundation walls; a plurality of lightweight conduit molds installed within the plurality of foundation concrete molds in a unique order of locations designated for conduits within the building foundation; wherein each conduit mold comprises a unitary cylindrical shape, a cylindrical central ring surrounding the cylindrical shape, and a rubber surface on each end of the cylindrical shape; wherein the foundation concrete mix is poured in the plurality of foundation concrete forms around the plurality of conduit molds and sets; wherein the foundation concrete mix sets to form the building foundation walls and simultaneously form the conduit holes at each of the plurality of concrete molds, wherein the plurality of foundation concrete forms are removed, and the rubber surfaces on each end of each cylindrical shape are substantially flush with interior and exterior surfaces of the building foundation walls; and removing the conduit mold from the building foundation to open a conduit hole without vibrating the building foundation or the foundation walls, and installing a conduit within the conduit hole in the foundation wall.

The subject invention also discloses a construction system for pre-casting conduit holes in a building foundation, the system comprising: a plurality of concrete molds installed around a location of the building foundation for supporting pouring of a foundation concrete mix; a plurality of lightweight conduit molds installed within the plurality of concrete molds at locations designated for conduits within the building foundation; wherein each conduit mold comprises a unitary cylindrical bar, a cylindrical central ring surrounding the cylindrical bar, and a rubber surface on each each of the cylindrical bar; wherein the foundation concrete is poured in the concrete forms around the plurality of conduit molds and sets; wherein the concrete forms are removed, and the rubber surfaces of each cylindrical bar are substantially flush with an interior and exterior wall of the building foundation; and removing the conduit mold from the foundation, and installing a conduit within the conduit hole in the foundation wall immediately, or for future use.

The subject invention discloses a foundation construction system for configuring conduit holes in a building foundation, the system comprising: a plurality of foundation molds installed around a location for the building foundation, wherein the plurality of foundation molds are configured to support a poured concrete mix; a plurality of cylindrical molds installed within the plurality of foundation molds at locations designated for conduits within the building foundation; wherein each cylindrical mold comprises a unitary cylindrical shape, a cylindrical central ring surrounding the cylindrical shape, and a rubber surface on each end of the cylindrical shape; wherein the concrete mix is poured in the plurality of foundation forms around the plurality of cylindrical molds and sets; wherein the plurality of foundation forms are removed, and the rubber surfaces on each end of each cylindrical shape are substantially flush with an interior and exterior wall of the building foundation; and removing the cylindrical mold from the building foundation to open a conduit hole, and installing a conduit within the conduit hole in the foundation wall.

The subject invention further discloses a method for pre-casting conduit holes in a building foundation, the method comprising: a) installing a plurality of concrete molds around the building foundation, wherein the plurality of concrete molds are configured to support a poured foundation concrete mix; b) installing a plurality of lightweight conduit molds within the plurality of concrete molds at locations designated for conduits within the building foundation, wherein each conduit mold comprises a unitary cylindrical bar, a cylindrical central ring surrounding the cylindrical bar, and a rubber surface on each end of the cylindrical bar; c) pouring the foundation concrete mix in the plurality of concrete forms around the plurality of conduit molds; d) setting the foundation concrete mix; e) removing the plurality of concrete forms, wherein the rubber surfaces of each cylindrical bar are substantially flush with an interior and exterior wall of the building foundation; f) removing the conduit mold from the building foundation to open a conduit hole; and g) installing a conduit within the conduit hole in the building foundation.

The subject invention also discloses a method for configuring conduit holes in a building foundation, the method comprising: a) installing a plurality of foundation molds around a location for the building foundation, wherein the plurality of foundation molds are configured to support a poured concrete mix; b) installing a plurality of cylindrical molds within the plurality of foundation molds at locations designated for conduits within the building foundation, wherein each cylindrical mold comprises a unitary cylindrical shape, a cylindrical central ring surrounding the cylindrical shape, and a rubber surface on each end of the cylindrical shape; c) pouring the concrete mix in the plurality of foundation forms around the plurality of cylindrical molds; d) setting the concrete mix; e) removing the plurality of foundation forms, wherein the rubber surfaces of each cylindrical shape are substantially flush with an interior and exterior wall of the building foundation; f) removing the cylindrical mold from the building foundation to open a conduit hole; and g) installing a conduit within the conduit hole in the building foundation.

The subject invention discloses a method for pre-casting conduit holes in a building foundation, the method comprising: a) installing a plurality of concrete molds around a location of the building foundation for supporting pouring of a foundation concrete mix; b) installing a plurality of lightweight conduit molds within the plurality of concrete molds at locations designated for conduits within the building foundation, wherein each conduit mold comprises a unitary cylindrical bar, a cylindrical central ring surrounding the cylindrical bar, and a rubber surface on each each of the cylindrical bar; c) pouring the foundation concrete mix in the concrete forms around the plurality of conduit molds; d) setting the foundation concrete mix; e) removing the concrete forms, wherein the rubber surfaces of each cylindrical bar are substantially flush with an interior and exterior wall of the building foundation; f) removing the conduit mold from the building foundation to open a conduit hole; and g) installing a conduit within the conduit hole in the building foundation.

A method for pre-casting conduit holes in a building foundation, the method comprising: a) installing a plurality of foundation concrete molds around a designated location of the building foundation, wherein the plurality of concrete molds are configured to support a poured foundation concrete mix to form the building foundation walls; b) installing a plurality of lightweight conduit molds within the plurality of foundation concrete molds at locations designated for conduits within the building foundation, wherein each conduit mold comprises a unitary cylindrical shape, a cylindrical central ring surrounding the cylindrical shape, and a rubber surface on each end of the cylindrical shape; c) pouring the foundation concrete mix in the plurality of foundation concrete forms around the plurality of conduit molds; d) setting the foundation concrete mix to form building foundation walls ; e) removing the plurality of foundation concrete forms, wherein the rubber surfaces of each cylindrical shape are substantially flush with interior and exterior surfaces of the building foundation walls; f) removing the conduit mold from the building foundation to open a conduit hole; and g) installing a conduit within the conduit hole in the building foundation.

A method for pre-casting conduit holes in a building foundation, the method comprising: a) installing a plurality of foundation concrete molds around a designated location of the building foundation, wherein the plurality of concrete molds are configured to support a poured foundation concrete mix to form the building foundation walls; b) installing a plurality of lightweight conduit molds within the plurality of foundation concrete molds at locations designated for conduits within the building foundation, wherein each conduit mold comprises a unitary cylindrical shape, a cylindrical central ring surrounding the cylindrical shape, and a rubber surface on each end of the cylindrical shape; c) pouring the foundation concrete mix in the plurality of foundation concrete forms around the plurality of conduit molds; d) setting the foundation concrete mix to form building foundation walls ; e) removing the plurality of foundation concrete forms, wherein the rubber surfaces of each cylindrical shape are substantially flush with interior and exterior surfaces of the building foundation walls; f) removing the conduit mold from the building foundation to open a conduit hole without drilling; and g) installing a conduit within the conduit hole in the building foundation.

A method for pre-casting conduit holes in a building foundation, the method comprising: a) installing a plurality of foundation concrete molds around a designated location of the building foundation, wherein the plurality of concrete molds are configured to support a poured foundation concrete mix to form the building foundation walls; b) installing a plurality of lightweight conduit molds within the plurality of foundation concrete molds at locations designated for conduits within the building foundation, wherein each conduit mold comprises a unitary cylindrical shape, a cylindrical central ring surrounding the cylindrical shape, and a rubber surface on each end of the cylindrical shape; c) pouring the foundation concrete mix in the plurality of foundation concrete forms around the plurality of conduit molds; d) setting the foundation concrete mix to form building foundation walls ; e) removing the plurality of foundation concrete forms, wherein the rubber surfaces of each cylindrical shape are substantially flush with interior and exterior surfaces of the building foundation walls; f) removing the conduit mold from the building foundation to open a conduit hole without vibrating the building foundation; and g) installing a conduit within the conduit hole in the building foundation.

A method for pre-casting conduit holes in a building foundation, the method comprising: a) installing a plurality of foundation concrete molds around a designated location of the building foundation, wherein the plurality of concrete molds are configured to support a poured foundation concrete mix to form the building foundation walls; b) installing a plurality of lightweight conduit molds within the plurality of foundation concrete molds at locations designated for conduits within the building foundation, wherein each conduit mold comprises a unitary cylindrical shape, a cylindrical central ring surrounding the cylindrical shape, and a rubber surface on each end of the cylindrical shape; c) pouring the foundation concrete mix in the plurality of foundation concrete forms around the plurality of conduit molds; d) setting the foundation concrete mix to form building foundation walls ; e) removing the plurality of foundation concrete forms, wherein the rubber surfaces of each cylindrical shape are substantially flush with interior and exterior surfaces of the building foundation walls; f) removing the conduit mold from the building foundation to open a conduit hole without either vibrating, drilling, hammering, or chiseling the building foundation or the foundation walls; and g) installing a conduit within the conduit hole in the building foundation.

A method for pre-casting conduit holes in a building foundation, the method comprising: a) installing a plurality of foundation concrete molds around a designated location of the building foundation, wherein the plurality of concrete molds are configured to support a poured foundation concrete mix to form the building foundation walls; b) installing a plurality of lightweight conduit molds within the plurality of foundation concrete molds at locations designated for conduits within the building foundation, wherein each conduit mold comprises a unitary cylindrical shape, a cylindrical central ring surrounding the cylindrical shape, and a rubber surface on each end of the cylindrical shape; c) pouring the foundation concrete mix in the plurality of foundation concrete forms around the plurality of conduit molds; d) setting the foundation concrete mix to form building foundation walls and simultaneously form the conduit holes at each of the plurality of concrete molds; e) removing the plurality of foundation concrete forms, wherein the rubber surfaces of each cylindrical shape are substantially flush with interior and exterior surfaces of the building foundation walls; f) removing the conduit mold from the building foundation to open a conduit hole without either vibrating, drilling, hammering, or chiseling the building foundation or the foundation walls; and g) installing a conduit within the conduit hole in the building foundation.

A method for pre-casting conduit holes in a building foundation, the method comprising: a) installing a plurality of foundation concrete molds around a designated location of the building foundation; b) configuring the plurality of concrete molds to support a poured foundation concrete mix that will form the building foundation walls; c) installing a plurality of lightweight conduit molds within the plurality of foundation concrete molds in a unique order of locations designated for conduits within the building foundation, wherein each conduit mold comprises a unitary cylindrical shape, a cylindrical central ring surrounding the cylindrical shape, and a rubber surface on each end of the cylindrical shape; d) pouring the foundation concrete mix in the plurality of foundation concrete forms around the plurality of conduit molds; e) setting the foundation concrete mix to form the building foundation walls and simultaneously form the conduit holes at each of the plurality of concrete molds; f) removing the plurality of foundation concrete forms, wherein the rubber surfaces of each cylindrical shape are substantially flush with interior and exterior surfaces of the building foundation walls; g) removing the conduit mold from the building foundation to open a conduit hole without either vibrating, drilling, hammering, or chiseling the building foundation or the foundation walls; and h) installing a conduit within the conduit hole in the building foundation.

In embodiments of the subject invention, the conduit mold may be removed from the foundation wall through drilling.

In further embodiments of the subject invention, the conduit mold may be removed from the foundation wall through melting with an acetone based solution.

In other embodiments of the subject invention, the conduit mold may remain in the foundation wall indefinitely without substantially destabilizing the foundation wall.

In additional embodiments of the subject invention, the conduit hole may be used as a conduit from the group of lines consisting of power lines, low voltage lines, cable lines, telephone lines, water supply, sewage, line sets condensers, and heat pumps.

In embodiments of the subject invention, the rubber ends of the conduit mold provide a substantially water tight seal on the the foundation until the mold is removed.

In further embodiments of the subject invention, the conduit mold may be composed of a material selected from the group of consisting of high density Styrofoam, Polystyrene Foam (both EPS and XPS), Polystyrene Plastic, Polystyrene Film, Polyisocyanurate ISO, Polyvinyl Chloride (PVC), Chlorinated Polyvinyl Chloride (CPVC), Unplasticide Polyvinyl Chloride(UPVC), Natural Isoprene, Ethylene Propylene Diene (EPDM), Nitrile Rubber (NBR), Styrene Butadiene Rubber (SBR), Silicone Rubber, Butyl Rubber, Polybutadiene, Aflas, Hypalon Rubber, Epichlorohydrin Rubber, Polyurethane, Polyethylene, lightweight solid wood, plywood, and fire retardant foams.

In other embodiments of the subject invention, the cylindrical bar of the conduit mold comprises diameters of 1.5" to 58".

In additional embodiments of the subject invention, the cylindrical bar of the conduit mold comprises lengths of 4" to 48".

In embodiments of the subject invention, the term "substantially" is defined as at least close to (and can include) a given value or state, as understood by a person of ordinary skill in the art. In one embodiment, the term "substantially" refers to ranges within 10%, preferably within 5%, more preferably within 1%, and most preferably within 0.1% of the given value or state being specified.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

These together with other objects of the invention, along with the various features of novelty, which characterize the invention, are pointed out with particularity in the claims annexed to and forming a part of this disclosure.

BRIEF DESCRIPTION OF THE DRAWINGS

Advantages of the present invention will be apparent from the following detailed description of embodiments thereof, which description should be considered in conjunction with the accompanying drawings, in which.

DETAILED DESCRIPTION OF THE EMBODIMENTS

While several variations of the present invention have been illustrated by way of example in particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

The subject invention discloses a method of constructing multiple conduits 1 in a residential and commercial building foundations 2 that eliminates the process of core drilling to produce conduits 1 after the foundation 2 has been poured and set. This process also creates optional openings 3 with insulated, water tight, fire retardant locations for possible future connections at a fraction of the cost of core drilling. Multiple watertight uninterrupted openings 3 from the interior of the foundation 2 to the exterior of the foundation 2 can be constructed using the subject method. These openings 3 can be used to install power and fluid conduits 1 for the building.

Figure 4:
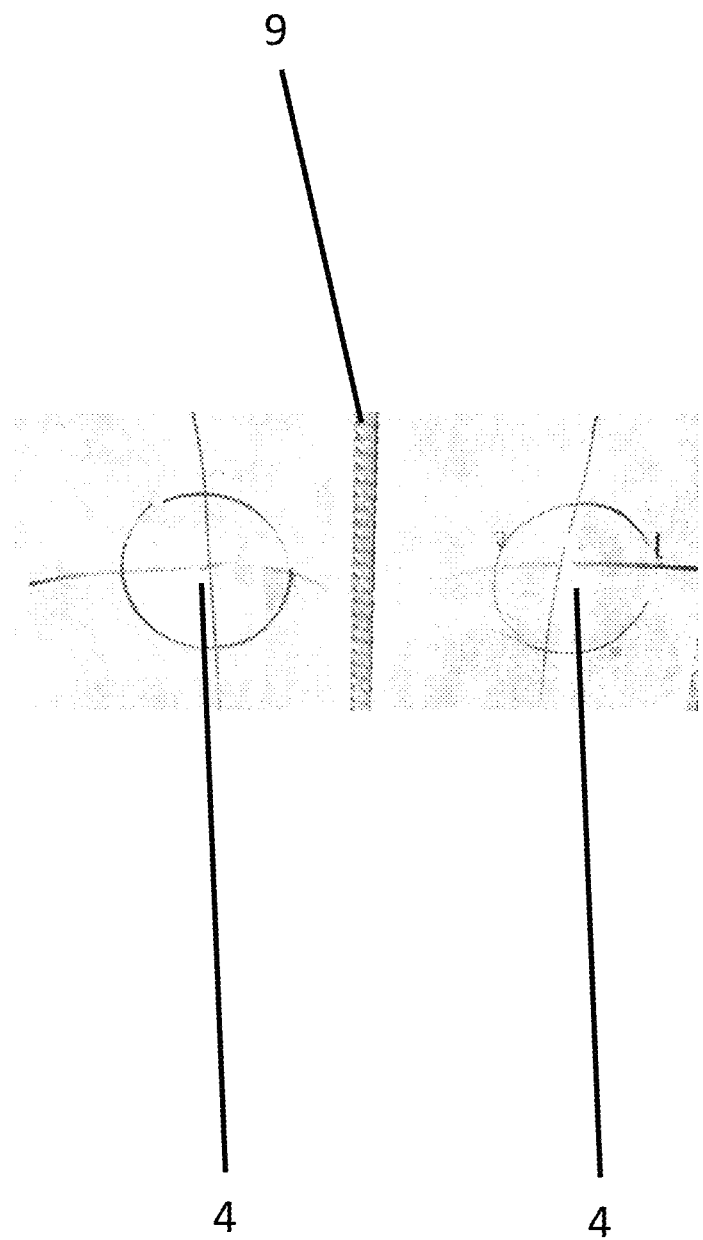
FIG. 4 illustrates marked positions in the foundation for placing lightweight conduit molds in advance of pouring the concrete over the concrete forms.
Figure 5:
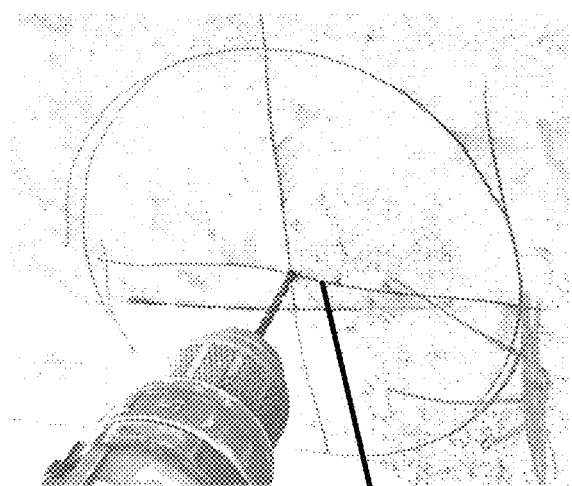
FIG. 5 illustrates marked positions in the foundation for placing lightweight conduit molds in advance of pouring the concrete over the concrete forms.

In the subject method, as illustrated in FIGS. 4 and 5, the positions 4 of the conduits 1 in the foundation 2 are determined in advance of pouring the concrete. In embodiments of the subject invention, multiple conduits 1 may be at locations at different positions of the foundation 2, as needed by the specific building construction.

Figure 1:
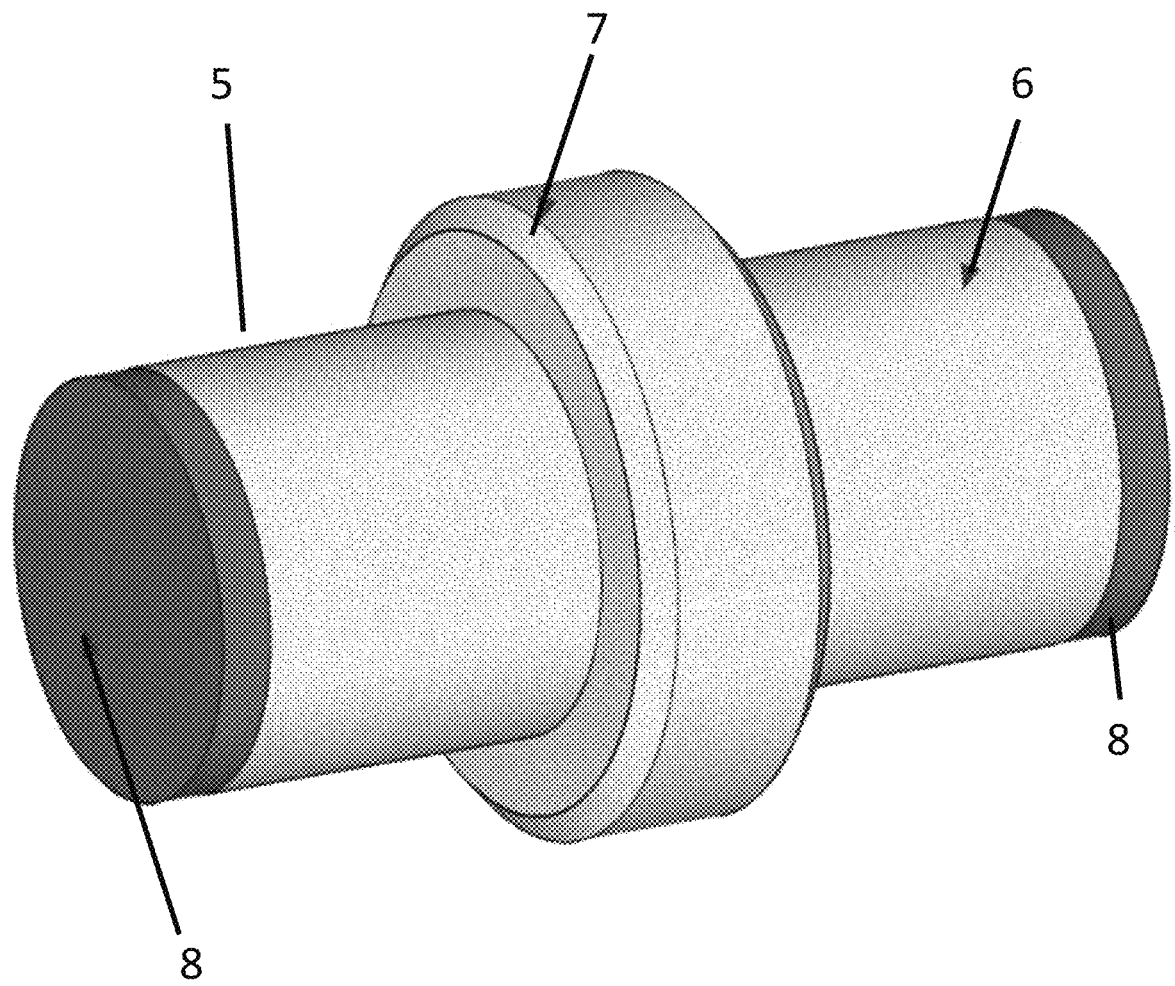
FIG. 1 illustrates a perspective view of a lightweight conduit mold for creating pre-cast holes in a building foundation.
Figure 2:
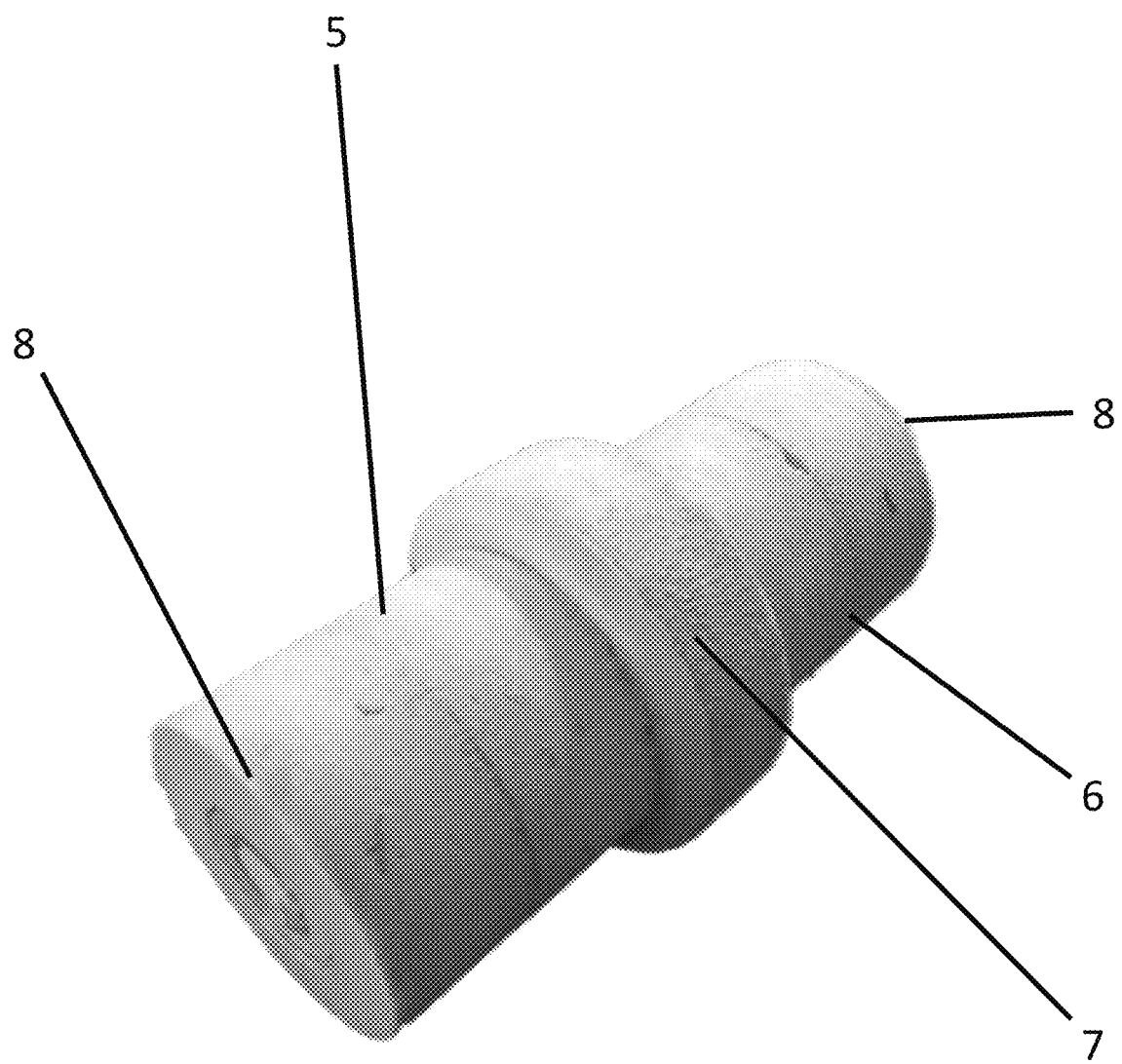
FIG. 2 illustrates another perspective view of the lightweight conduit mold for creating pre-cast holes in a building foundation.
Figure 3:
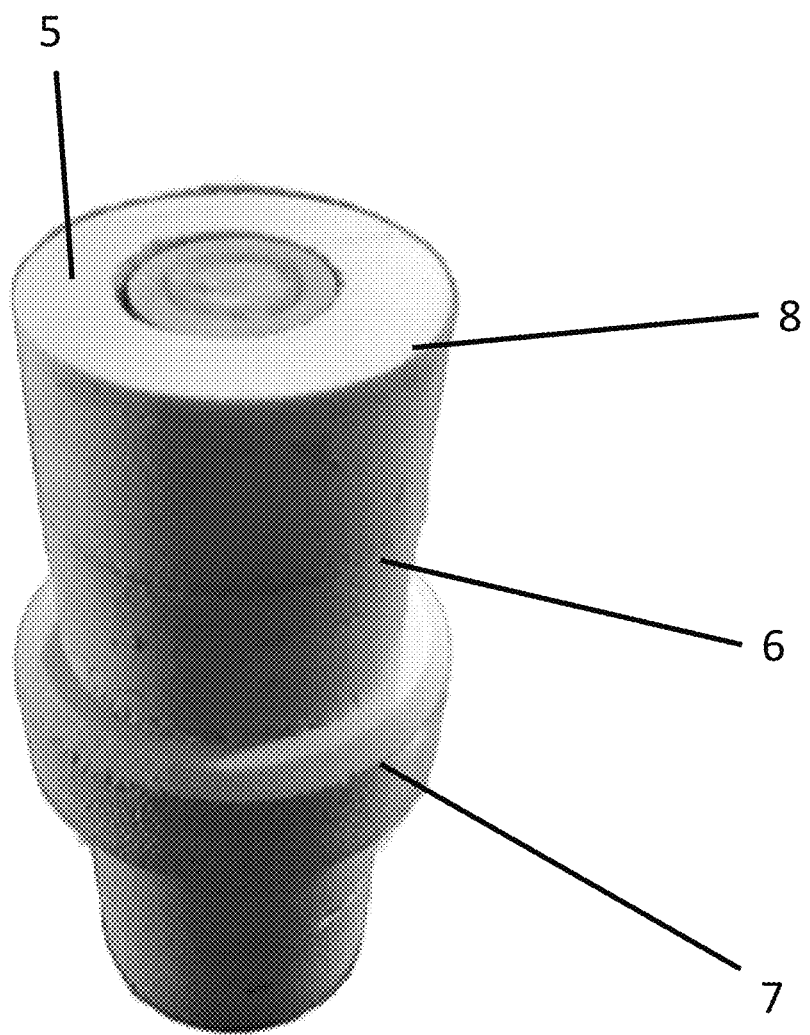
FIG. 3 illustrates a top view of the lightweight conduit mold for creating pre-cast holes in a building foundation.
Figure 6:
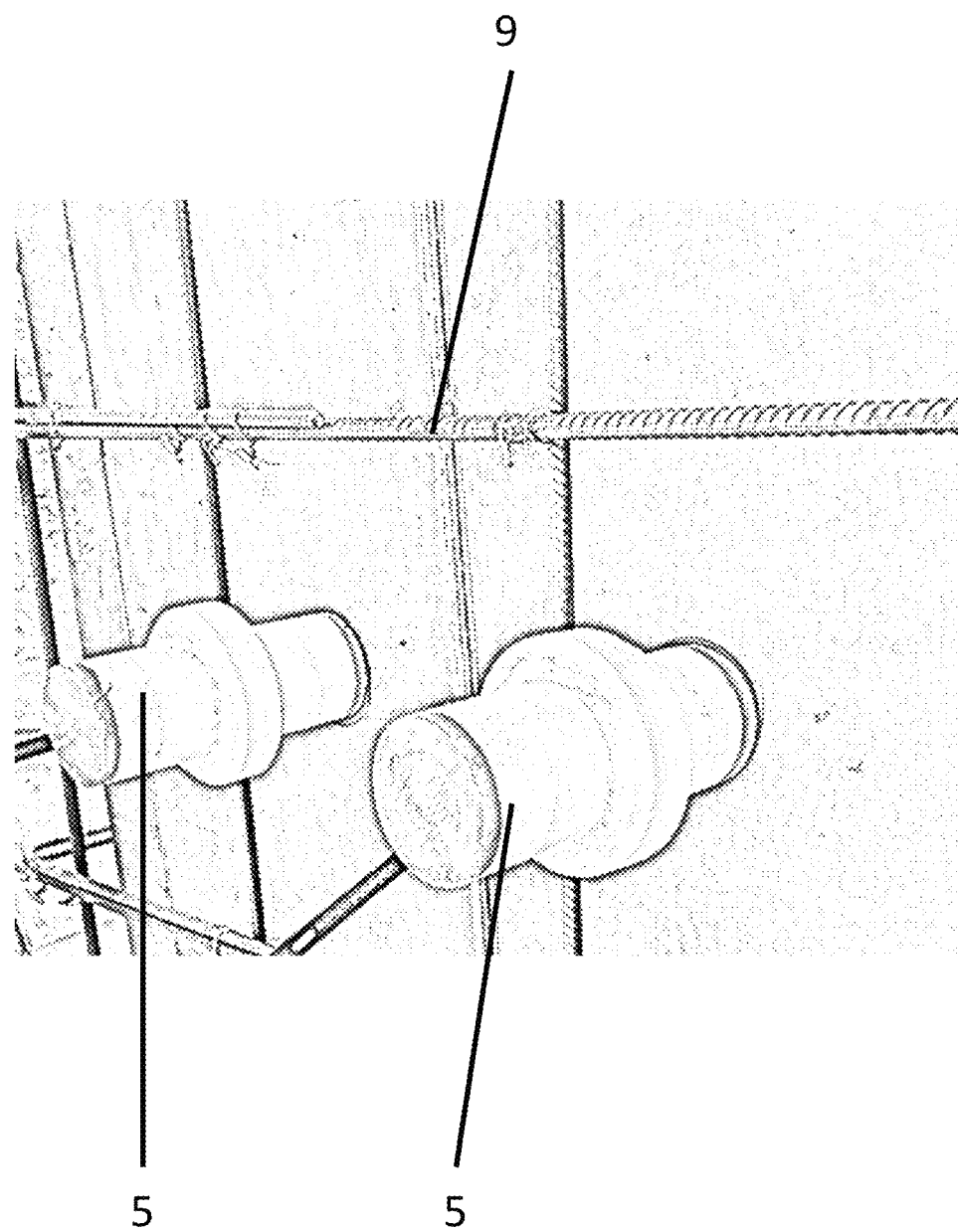
FIG. 6 illustrates lightweight conduit molds attached to the concrete forms in pre-determined positions in advance of pouring the concrete over the conduit molds and the concrete forms.

At each selected conduit location 4, as illustrated in FIG. 6, a lightweight conduit mold 5 is installed before the foundation concrete is poured. As illustrated in FIGS. 1-3, each conduit mold 5 is comprised of a unitary cylinder 6, a ring 7 with a larger diameter centered on the mold 5, and two thick rubber ends 8 on each side of the unitary cylinder 6.

The rubber ends 8 of each conduit mold 5 secure the mold to concrete forms 9 during the concrete pour. The rubber ends 8 also provide a watertight seal on each end of the conduit mold 5 after the foundation 2 has cured.

As the foundation concrete is poured, it surrounds each pre-installed conduit mold 5. The larger rings 7 of each conduit mold 5 lock it into the foundation 2 concrete at the pre-installed location 4, as the concrete cures and sets.

Figure 7:
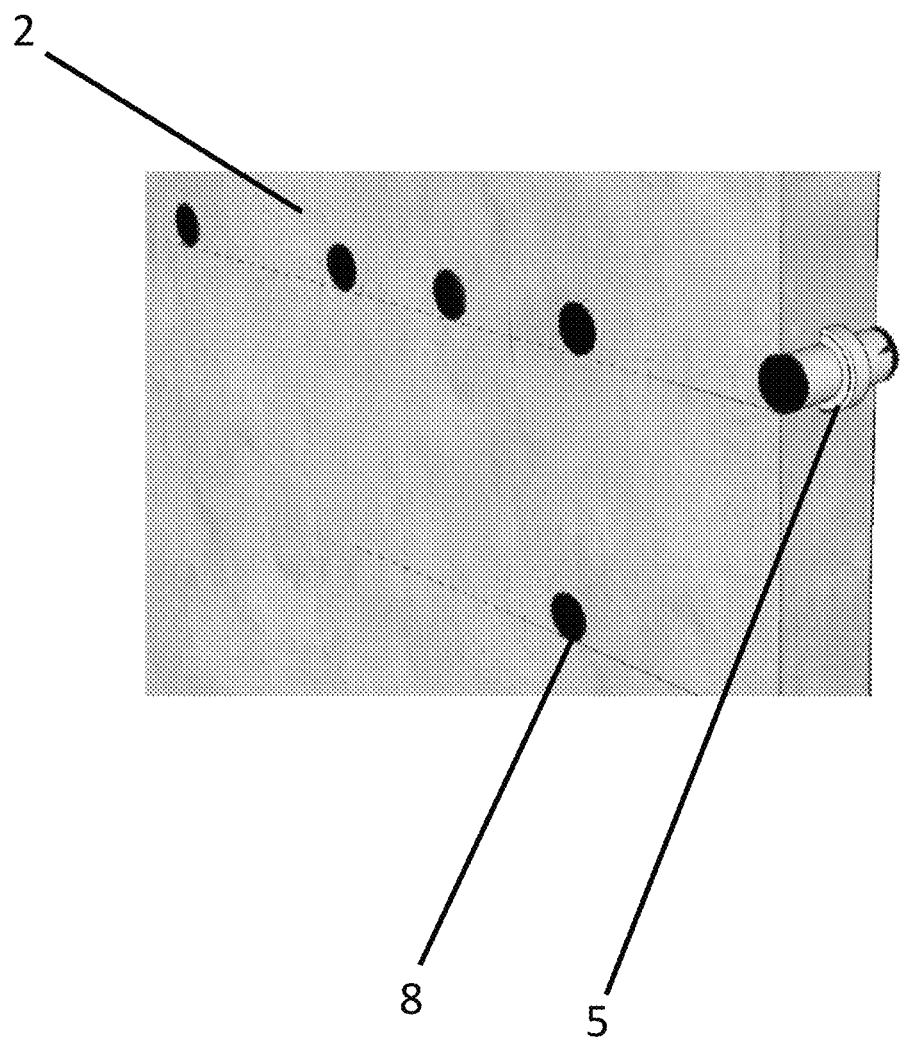
FIG. 7 illustrates a perspective view of a cast building foundation with installed lightweight conduit molds.
Figure 8:
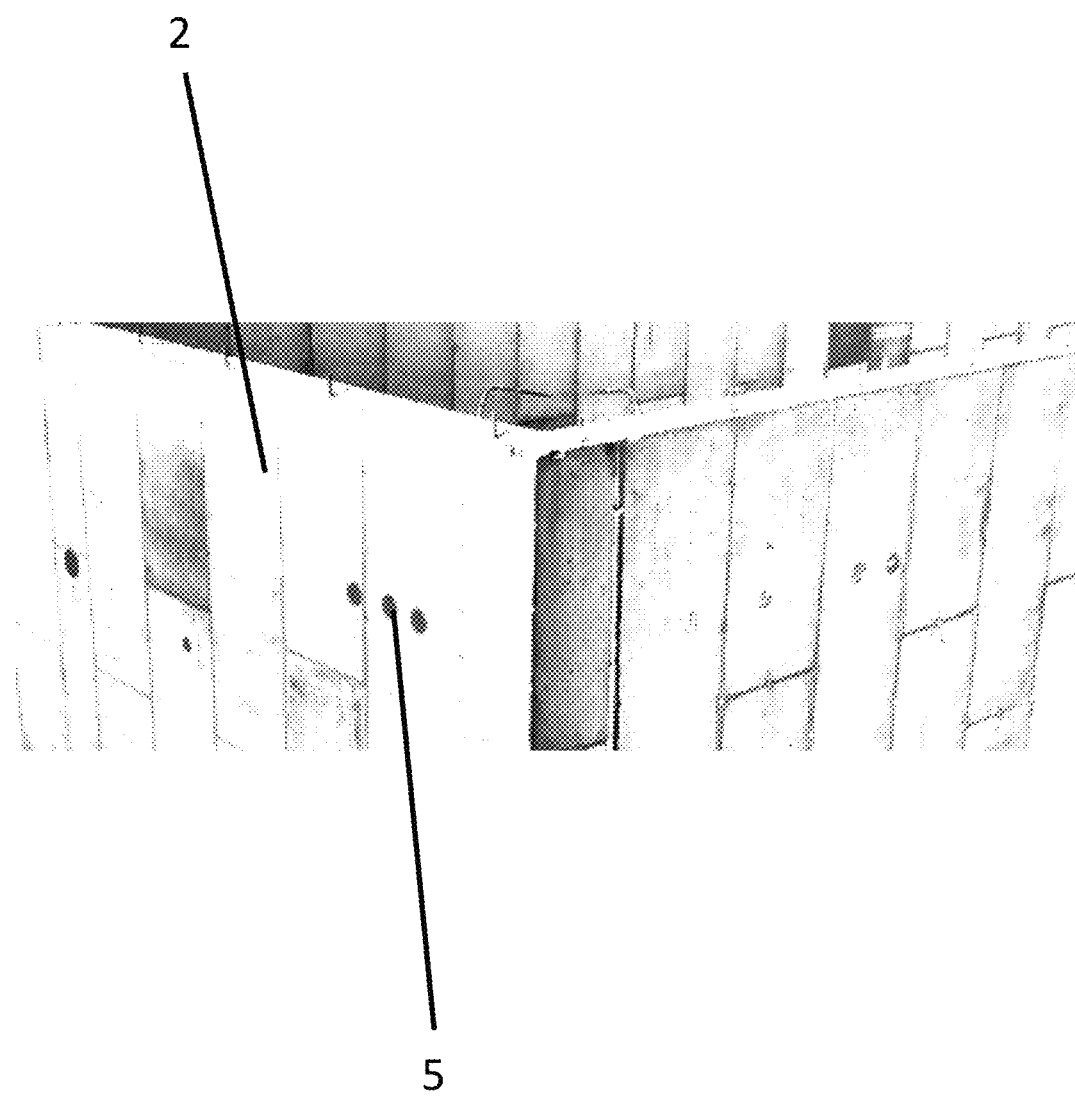
FIG. 8 illustrates a perspective view of a cast building foundation with installed lightweight conduit molds.

As illustrated in FIGS. 7 and 8, once the foundation concrete has set, the concrete forms 9 are removed, and the rubber ends 8 of the conduit mold 5 are flush with the interior and exterior walls of the foundation 2. The rubber ends 8 provide a water tight seal on the conduit mold 5 in the foundation until the hole 3 is exposed for use.

Figure 9:
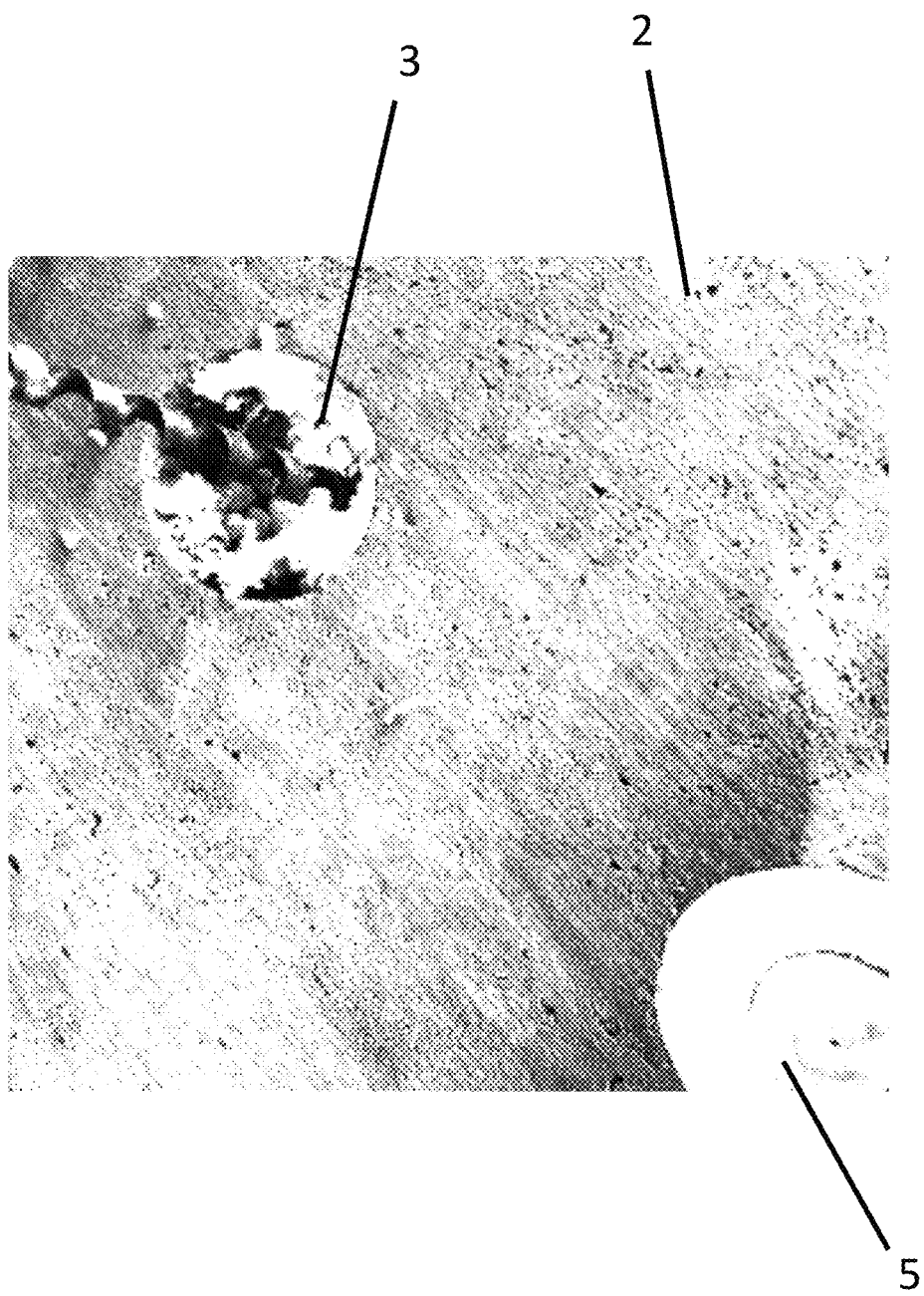
FIG. 9 illustrates a perspective view of an installed lightweight conduit mold being drilled out of a cast building foundation.
Figure 10:
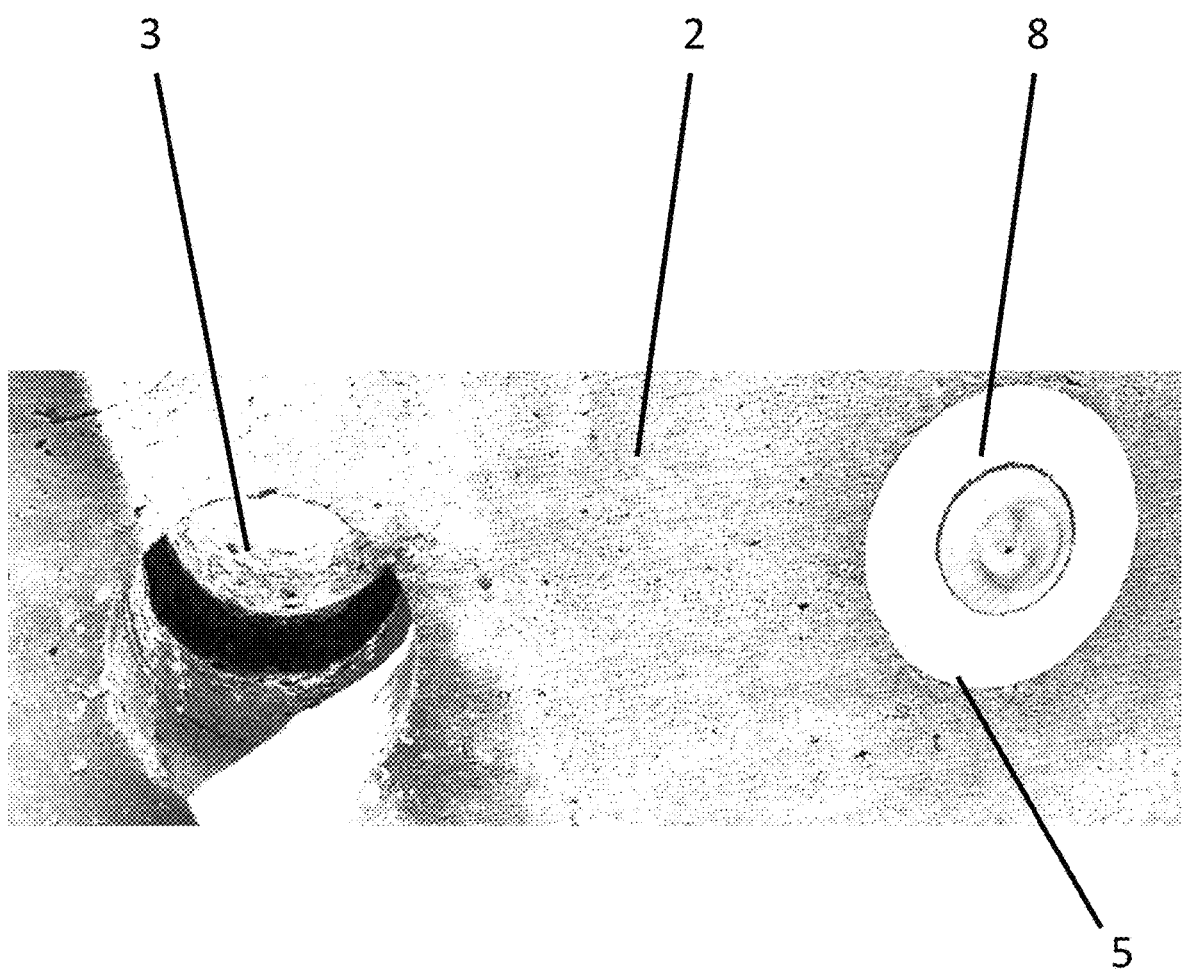
FIG. 10 illustrates a perspective view of an installed lightweight conduit mold and a hole from a removed lightweight conduit mold in a building foundation.
Figure 11:
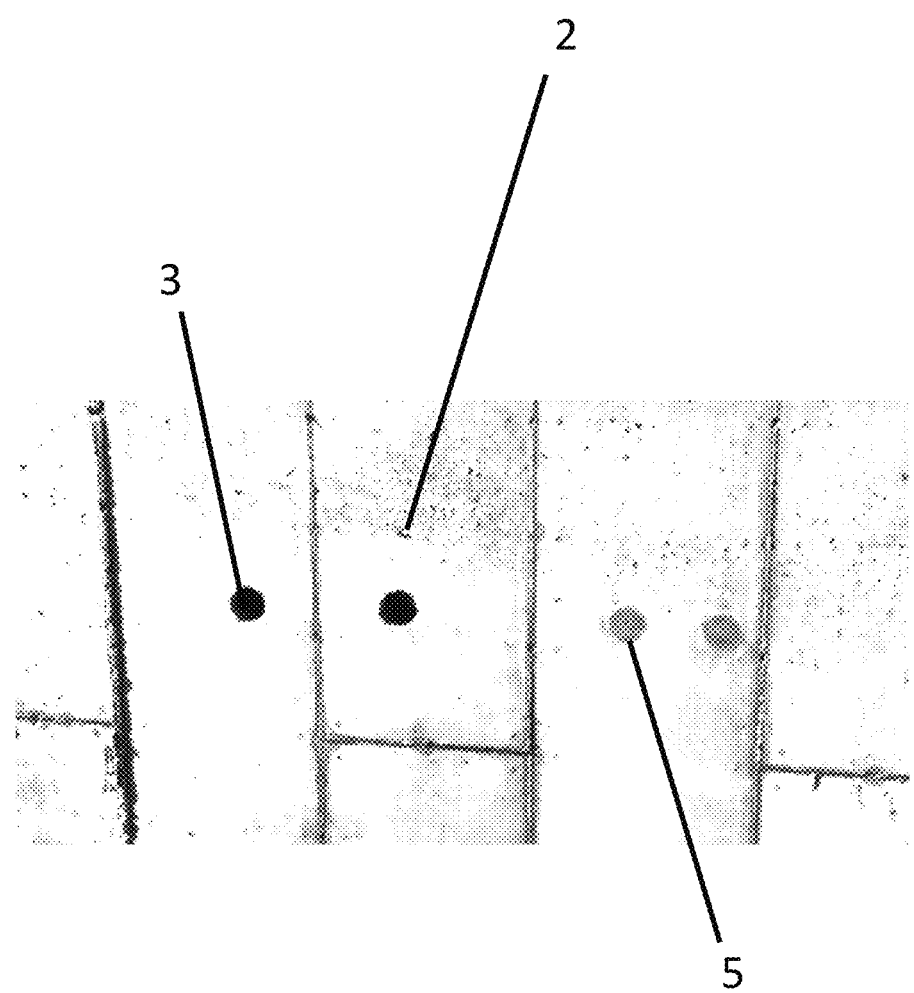
FIG. 11 illustrates a perspective view of installed lightweight conduit molds and holes from a removed lightweight conduit molds in a building foundation.
Figure 12:
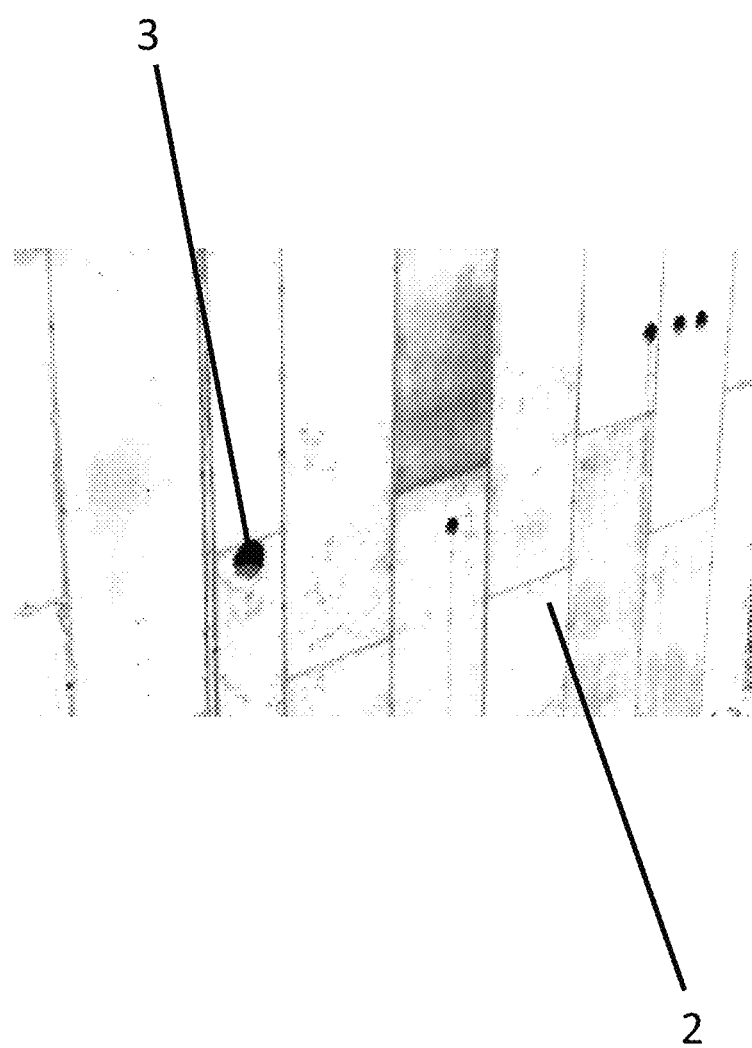
FIG. 12 illustrates a perspective view of installed lightweight conduit molds and holes from a removed lightweight conduit molds in a building foundation.

As illustrated in FIG. 9, when a conduit 1 is ready to be installed, the installed conduit mold 5 is drilled or melted out of the foundation 2 wall with an acetone based solution. The desired conduits 1 can then be installed in the remaining hole 3 and secured with whichever preferred method.

As illustrated in FIGS. 14-17, once the conduit holes 3 are drilled, and the mold 5 is removed, a cylindrical conduit 1 in placed within the resulting hole 3. A watertight seal is created around the conduit 1 using a link seal which contains a plurality of links and a gasket. As the link seal is tightened, the links compress the gasket to create a tight fitting between the concrete foundation 2 and the conduit 1.

Figure 13:
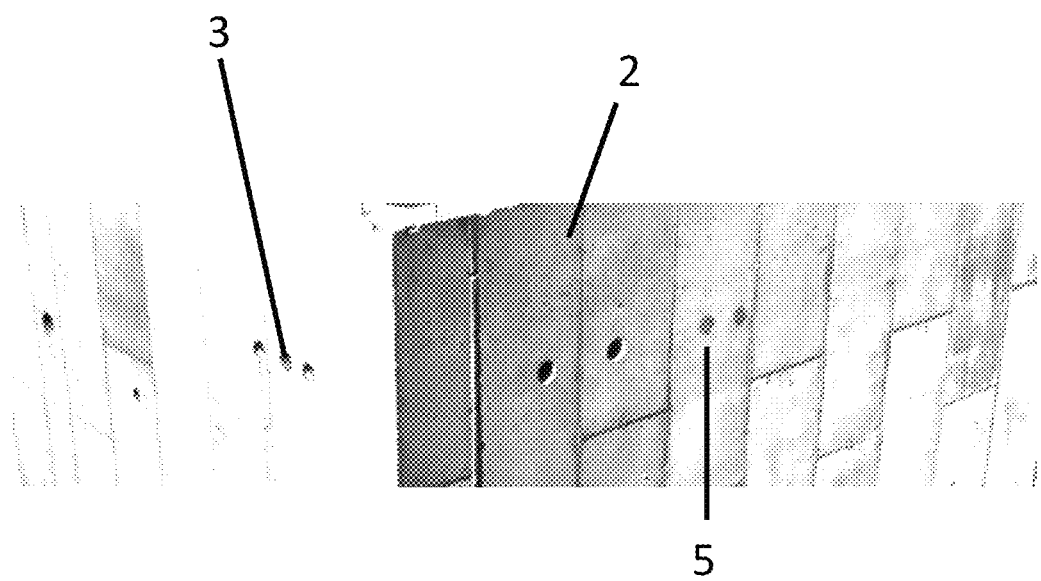
FIG. 13 illustrates a perspective view of installed lightweight conduit molds and holes from a removed lightweight conduit molds in a building foundation.
Figure 14:
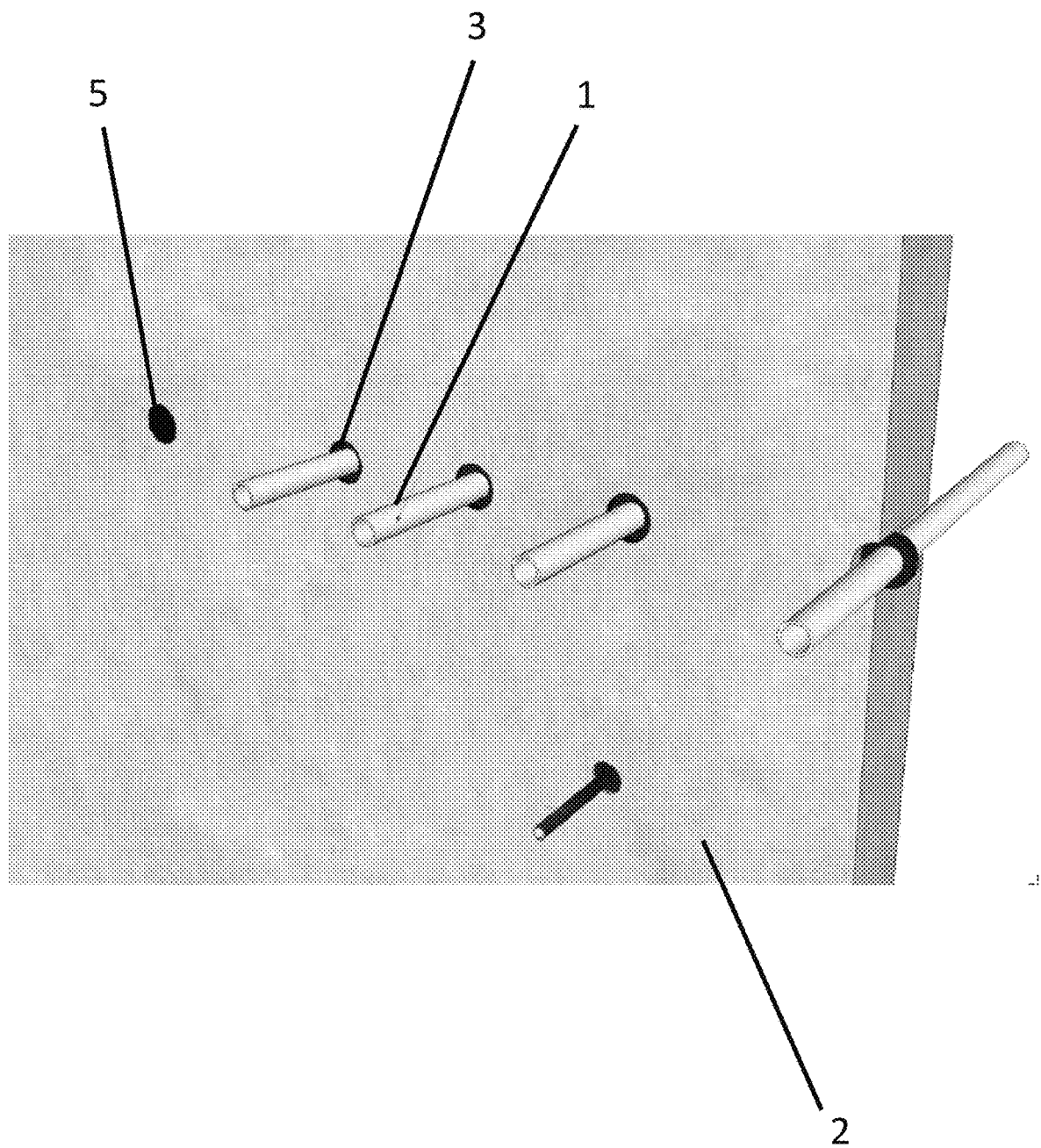
FIG. 14 illustrates a perspective view of multiple conduits inserted into a building foundation through holes from removed lightweight conduit molds and a lightweight conduit mold remaining installed in the foundation until later use.
Figure 15:
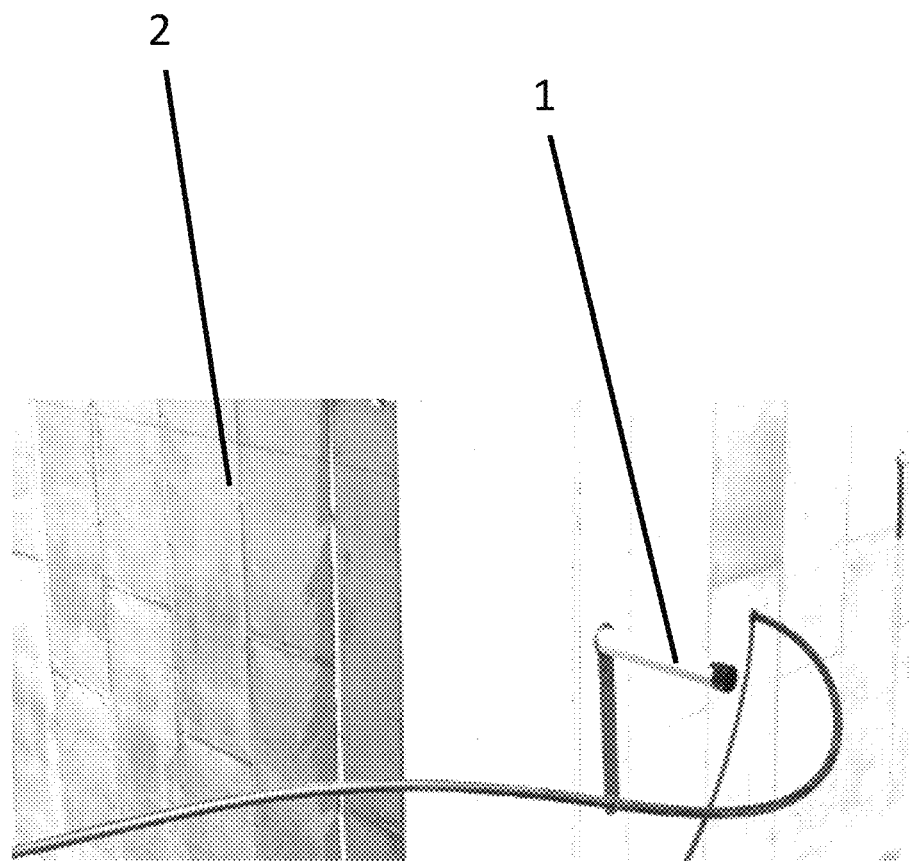
FIG. 15 illustrates a perspective view of multiple conduits inserted into a building foundation through holes from removed lightweight conduit molds
Figure 16:
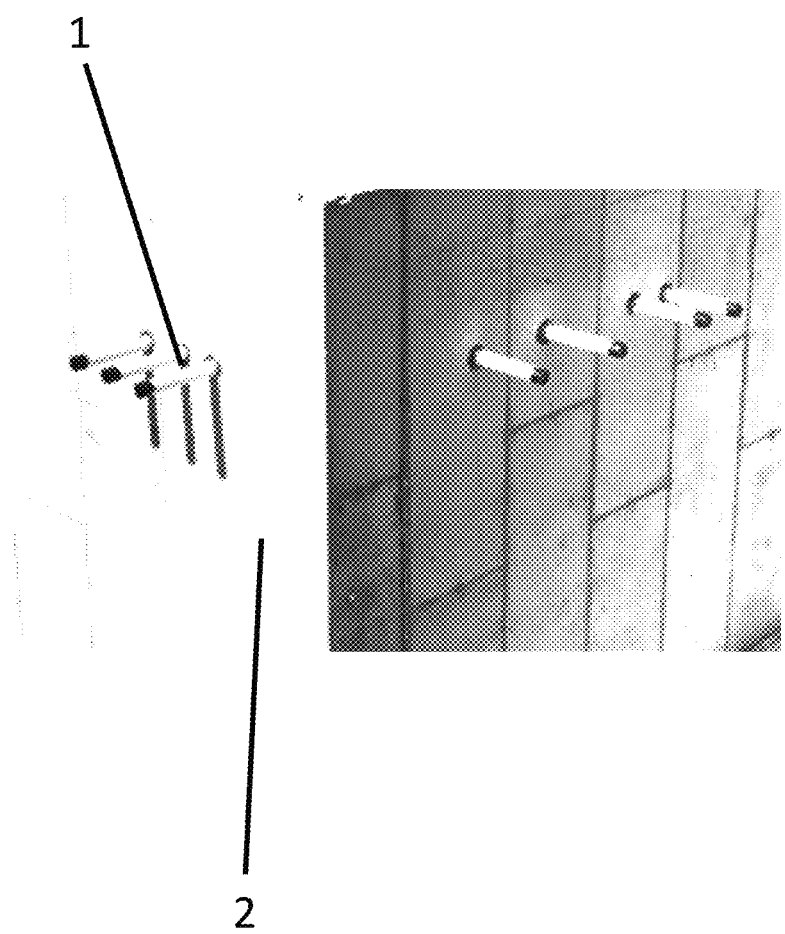
FIG. 16 illustrates a perspective view of multiple conduits inserted into a building foundation through holes from removed lightweight conduit molds.
Figure 17:
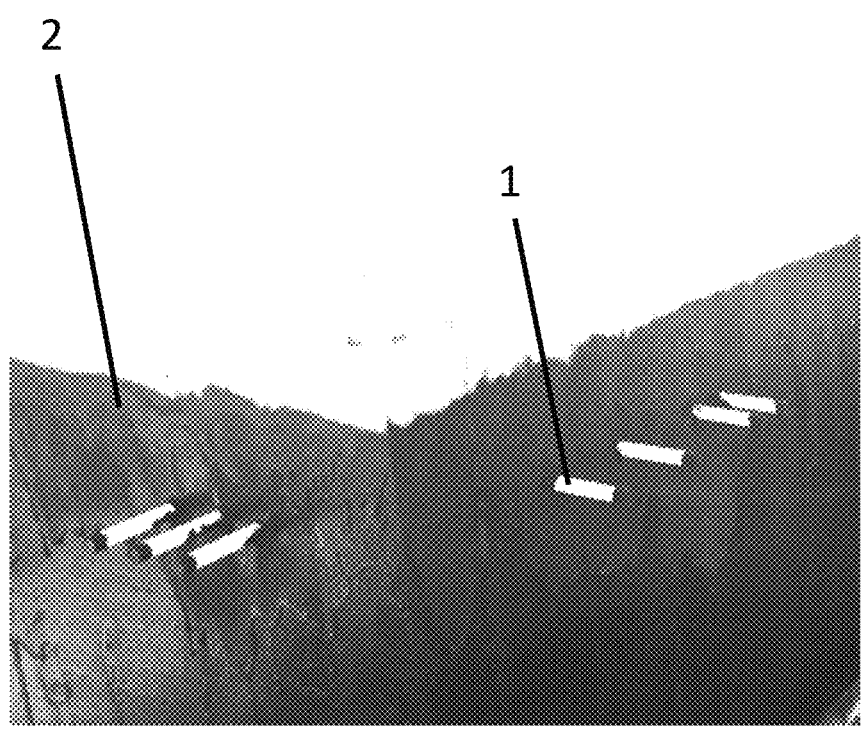
FIG. 17 illustrates a perspective view of multiple conduits inserted into a building foundation through holes from removed lightweight conduit molds.

As illustrated in FIGS. 13 and 14, if a hole 3 is not needed in the foundation 2 at a mold 5 location 4, the conduit mold 5 may be left in the foundation wall indefinitely without any repercussions.

In embodiments of the subject invention, the lightweight conduit mold 5 may be primarily composed of high density Styrofoam®, or other lightweight material that does not react with concrete, such as: Polystyrene Foam (both EPS and XPS), Polystyrene Plastic, Polystyrene Film, Polyisocyanurate ISO, Polyvinyl Chloride(PVC), Chlorinated Polyvinyl Chloride (CPVC), Unplasticide Polyvinyl Chloride (UPVC), Natural Isoprene, Ethylene Propylene Diene (EPDM), Nitrile Rubber (NBR), Styrene Butadiene Rubber (SBR), Silicone Rubber, Butyl Rubber, Polybutadiene, Aflas, Hypalon Rubber, Epichlorohydrin Rubber, Polyurethane, Polyethylene, lightweight solid wood, or plywood. In another embodiment of the subject invention, the lightweight conduit mold may be composed of fire resistant foam.

In embodiments of the subject invention the diameters of the lightweight conduit mold 5 range from 1.5" to 58". In further embodiments of the subject invention the lengths of the lightweight conduit mold 5 range from 4" to 48".

What is claimed is:

1. A method for pre-casting conduit holes in a building foundation, the method comprising:
    a) installing a plurality of concrete molds around the building foundation, wherein the plurality of concrete molds are configured to support a poured foundation concrete mix;
    b) installing a plurality of lightweight conduit molds within the plurality of concrete molds at locations designated for conduits within the building foundation, wherein each conduit mold comprises a unitary cylindrical bar, a cylindrical central ring surrounding the cylindrical bar, and a rubber surface on each end of the cylindrical bar;
    c) pouring the foundation concrete mix in the plurality of concrete forms around the plurality of conduit molds;
    d) setting the foundation concrete mix;
    e) removing the plurality of concrete forms, wherein the rubber surfaces of each cylindrical bar are substantially flush with an interior and exterior wall of the building foundation;
    f) removing the conduit mold from the building foundation to open a conduit hole; and
    g) installing a conduit within the conduit hole in the building foundation, wherein the conduit mold is removed from the foundation wall through drilling.

2. The method of claim 1, wherein the conduit mold remains in the foundation wall indefinitely without substantially destabilizing the foundation wall.

3. The method of claim 1, wherein the conduit hole is a conduit for a group of lines consisting of power lines, low voltage lines, cable lines, telephone lines, water supply, sewage, line sets condensers, heat pumps, or any other utility line.

4. The method of claim 1, wherein the rubber ends of the conduit mold provide a substantially water tight seal on the the foundation until the conduit mold is removed.

5. The method of claim 1, wherein the conduit mold is composed of a material selected from the a group of consisting of high density Styrofoam, Polystyrene Foam (both EPS and XPS), Polystyrene Plastic, Polystyrene Film, Polyisocyanurate ISO, Polyvinyl Chloride (PVC), Chlorinated Polyvinyl Chloride (CPVC), Unplasticide Polyvinyl Chloride(UPVC), Natural Isoprene, Ethylene Propylene Diene (EPDM), Nitrile Rubber (NBR), Styrene Butadiene Rubber (SBR), Silicone Rubber, Butyl Rubber, Polybutadiene, Aflas, Hypalon Rubber, Epichlorohydrin Rubber, Polyurethane, Polyethylene, lightweight solid wood, plywood, and fire retardant foams.

6. The method of claim 1, wherein the cylindrical bar of the conduit mold comprises diameters of 1.5 to 58 inches.

7. The method of claim 1, wherein the cylindrical bar of the conduit mold comprises lengths of 4 to 48 inches.

8. A method for pre-casting conduit holes in a building foundation, the method comprising:

a) installing a plurality of concrete molds around the building foundation, wherein the plurality of concrete molds are configured to support a poured foundation concrete mix;
b) installing a plurality of lightweight conduit molds within the plurality of concrete molds at locations designated for conduits within the building foundation, wherein each conduit mold comprises a unitary cylindrical bar, a cylindrical central ring surrounding the cylindrical bar, and a rubber surface on each end of the cylindrical bar;
c) pouring the foundation concrete mix in the plurality of concrete forms around the plurality of conduit molds;
d) setting the foundation concrete mix;
e) removing the plurality of concrete forms, wherein the rubber surfaces of each cylindrical bar are substantially flush with an interior and exterior wall of the building foundation;
f) removing the conduit mold from the building foundation to open a conduit hole; and
g) installing a conduit within the conduit hole in the building foundation, wherein the conduit mold is removed from the foundation wall through melting with an acetone based solution.

9. The method of claim 8, wherein the conduit mold remains in the foundation wall indefinitely without substantially destabilizing the foundation wall.

10. The method of claim 8, wherein the conduit hole is a conduit for a group of lines consisting of power lines, low voltage lines, cable lines, telephone lines, water supply, sewage, line sets condensers, heat pumps, or any other utility line.

11. The method of claim 8, wherein the rubber ends of the conduit mold provide a substantially water tight seal on the the foundation until the conduit mold is removed.

12. The method of claim 8, wherein the conduit mold is composed of a material selected from a group of consisting of high density Styrofoam, Polystyrene Foam (both EPS and XPS), Polystyrene Plastic, Polystyrene Film, Polyisocyanurate ISO, Polyvinyl Chloride(PVC), Chlorinated Polyvinyl Chloride (CPVC), Unplasticide Polyvinyl Chloride(UPVC), Natural Isoprene, Ethylene Propylene Diene (EPDM), Nitrile Rubber (NBR), Styrene Butadiene Rubber (SBR), Silicone Rubber, Butyl Rubber, Polybutadiene, Aflas, Hypalon Rubber, Epichlorohydrin Rubber, Polyurethane, Polyethylene, lightweight solid wood, plywood, and fire retardant foams.

13. The method of claim 8, wherein the cylindrical bar of the conduit mold comprises diameters of 1.5 to 58 inches.

14. The method of claim 8, wherein the cylindrical bar of the conduit mold comprises lengths of 4 to 48 inches.

* * * * *